United States Patent
Kobayashi et al.

[11] Patent Number: 6,043,303
[45] Date of Patent: Mar. 28, 2000

[54] HEXAGONAL CRYSTALS OF DIACETALS, NUCLEATING AGENT COMPRISING SAID HEXAGONAL CRYSTAL, POLYOLEFIN RESIN COMPOSITION AND MOLDING CONTAINING SAID HEXAGONAL CRYSTALS, AND METHOD FOR MOLDING SAID COMPOSITION

[75] Inventors: Toshiaki Kobayashi, Nara; Shizuyoshi Sakai, Hamamatsu, both of Japan

[73] Assignee: New Japan Chemical Co. Ltd., Kyoto, Japan

[21] Appl. No.: 08/894,961

[22] PCT Filed: Feb. 29, 1996

[86] PCT No.: PCT/JP96/00476

§ 371 Date: Sep. 3, 1997

§ 102(e) Date: Sep. 3, 1997

[87] PCT Pub. No.: WO96/27597

PCT Pub. Date: Sep. 12, 1996

[30] Foreign Application Priority Data

Mar. 3, 1995 [JP] Japan ................. 7-44429

[51] Int. Cl.[7] .............................. C08K 5/06
[52] U.S. Cl. .................. 524/109; 524/108; 524/110; 568/591
[58] Field of Search ...................... 524/108, 109, 524/110; 568/591

[56] References Cited

U.S. PATENT DOCUMENTS

| | | |
|---|---|---|
| 4,562,265 | 12/1985 | Machell . |
| 4,902,807 | 2/1990 | Kobayashi et al. .............. 549/364 |

FOREIGN PATENT DOCUMENTS

| | | |
|---|---|---|
| 57-32278 | 2/1982 | Japan . |
| 57-185288 | 11/1982 | Japan . |
| 58-180488 | 10/1983 | Japan . |
| 60-199891 | 10/1985 | Japan . |
| 1-149789 | 6/1989 | Japan . |
| 2-231488 | 9/1990 | Japan . |
| 3-120285 | 5/1991 | Japan . |
| 4-139189 | 5/1992 | Japan . |

*Primary Examiner*—David W. Wu
*Assistant Examiner*—K. C. Egwim
*Attorney, Agent, or Firm*—Larson & Taylor LLP

[57] ABSTRACT

This invention provides hexagonal crystals of a diacetal represented by the formula (1)

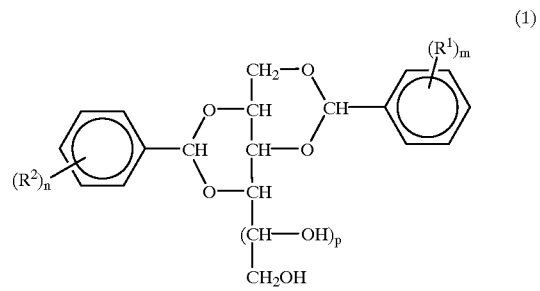

wherein $R^1$ and $R^2$ each represents an alkyl group having 1 to 4 carbon, atoms or a halogen atom, each of m and n is an integer of 0 to 2 and p is 0 or 1, a nucleating agent comprising the diacetal of the formula (1), wherein part or the whole of the diacetal is in the form of hexagonal crystals, a polyolefin resin composition and a molded product each comprising a polyolefin resin and the nucleating agent, and a method for molding the polyolefin resin composition.

According to the invention, the occurrence of fish eyes and coloration in a molded product can be prevented, the optical, mechanical and thermal properties of the molded product are superior and the molding cycle is shortened.

18 Claims, No Drawings

HEXAGONAL CRYSTALS OF DIACETALS, NUCLEATING AGENT COMPRISING SAID HEXAGONAL CRYSTAL, POLYOLEFIN RESIN COMPOSITION AND MOLDING CONTAINING SAID HEXAGONAL CRYSTALS, AND METHOD FOR MOLDING SAID COMPOSITION

TECHNICAL FIELD

The present invention relates to hexagonal crystals of diacetals useful as nucleating agents for polyolefin resins, a nucleating agent comprising said hexagonal crystals, and a polyolefin resin composition comprising said nucleating agent and a polyolefin resin. The present invention also concerns with a method for molding said polyolefin resin composition by injection molding or extrusion molding, and molded products produced from the composition via processing.

BACKGROUND ART

Conventionally diacetals such as 1,3:2,4-bis-O-(p-methylbenzylidene)-D-sorbitol and the like have been incorporated as a nucleating agent into polyolefin resins to improve the optical properties of the polyolefin resins such as transparency and gloss, their mechanical properties such as rigidity and their thermal properties (e.g. Japanese Unexamined Patent Publication No. 117044/1978).

However, the above-mentioned diacetal nucleating agent has posed problems of frequently developing fish eyes in the obtained molded products and coloring the molded products yellow. While polyolefin resins containing said diacetal nucleating agent are considerably improved in the above optical, mechanical and thermal properties compared with polyolefin resins free of the diacetal nucleating agent, there is a need for further improvements in optical, mechanical and thermal properties in view of the current growing demand for high qualities.

From the viewpoint of methods for molding polyolefin resins, problems are raised. That is, in high temperature melting molding methods, molded products tend to become yellowish, whereas in low temperature melting molding methods, fish eyes are easily formed due to a non-dispersed nucleating agent although the coloration of the molded products are suppressed.

An object of the present invention is to provide a nucleating agent which is capable of preventing the occurrence of the above-mentioned fish eyes and coloration and capable of increasing the molding speed and further improving the optical, mechanical and thermal properties of polyolefin resins, as well as a polyolefin resin composition and molded products containing such nucleating agent.

Another object of the invention is to provide a method for molding polyolefin resins substantially free of the foregoing prior art problems.

DISCLOSURE OF THE INVENTION

The present inventors carried out extensive research to achieve said objects. In the course of the research, the present inventors took an approach different from the conventional investigation which was limited to the chemical structure of diacetals, and continued the research paying attention to the crystal structure of diacetals.

As to the crystal structure of diacetals, it was already elucidated that a diacetal, when fully aged in a molten polyolefin, forms a fibril network. However, the relation of said network structure with the action of nucleating agents was not clear.

In particular, not only the relation of the network with the action of nucleating agents is unknown, but also fundamental questions are unresolved at all as to whether the diacetal network formed in a molten polyolefin is of molecular crystal or is amorphous and, if the network is crystalline, as to what the unit lattice thereof is like ("The Advanced Techniques of Additives for Polymers", published by Kabushiki Kaisha CMC on Jan. 6, 1988, pp 204–222 (Chapter 9, Nucleating Agent)).

"The Advanced Techniques of Additives for Polymers (published by Kabushiki Kaisha CMC on Jan. 6, 1988) referred to above describes on page 207 a structure of a freeze-dried product of a gel formed from a diacetal and a dioxane solvent, not a gel formed from a diacetal and a polymer. This freeze-dried product is not composed of hexagonal crystals of a diacetal but is composed of a hexagonally assembled structure of helically grown pillars. That is to say, said product is not a crystal composed of hexagonal unit lattices. It is also unknown whether said product is crystalline or amorphous.

In other words, the traditional researches on the nucleating agents have not gone farther than the proposals with respect to the chemical structure of the nucleating agents. Although the object of the researches has been directed to the crystal formation of polyolefin resins or the control of crystal morphology, the researches has been continued without knowing the relation with the crystal structure or amorphous structure of the diacetal nucleating agents which are deeply involved therein. Additionally, no investigation has been made on the manufacture of optimum nucleating agent crystals, including preferred crystal forms or non-crystalline forms of the diacetals and the chemical structure of the diacetal nucleating agent, and on the conditions for molding polyolefin resins depending on the crystal forms. Therefore, an optimum temperature for melting the resin was unclear and unavoidably set to a higher temperature than necessary or to an excessively low temperature.

Incidentally, an optimum cooling temperature in injection- or extrusion-molding a polyolefin resin has not been known, but it has been considered as a matter of course that the best way to minimize the cycle time or to maximize the molding efficiency is to set the cooling temperature of the mold or the roll to a temperature at which the polyolefin resin crystallizes at a maximum rate.

Under the circumstances, the present inventors conducted research on diacetal crystals, analyzed the structure of diacetal crystals by x-ray diffraction method, separately produced hexagonal and cubic crystals of diacetals and evaluated the properties of these crystals as a nucleating agent. As a result, the following novel findings were obtained.

(1) Diacetals have a wide variety of crystal structures, and there exist at least hexagonal crystals (which may be hereinafter referred to as "A") and cubic crystals (which may be hereinafter referred to as "B").

(2) As a nucleating agent for the formation of polyolefin crystals, hexagonal crystals (A) are by far superior in the performance to cubic crystals (B).

(3) Hexagonal crystals (A) are dispersed or dissolved in molten polyolefin at a higher rate than cubic crystals (B).

(4) Not only hexagonal crystals (A) but other kinds of crystals such as cubic crystals (B) have the property of bringing about a ramified fibril state crystal, and not spherulites or plate crystals.

(5) Hexagonal crystals can be produced, as described later, for example, when from a gel formed from a specific solvent, said solvent is evaporated, whereas other kinds of crystals than hexagonal crystals such as cubic crystals can be produced as by gradually cooling molten diacetal or by conventional methods of preparing a diacetal.

The present inventors completed the present invention based on the above-mentioned findings and additionally considering the results of further investigations.

The present invention provides hexagonal crystals of a diacetal represented by the formula (1)

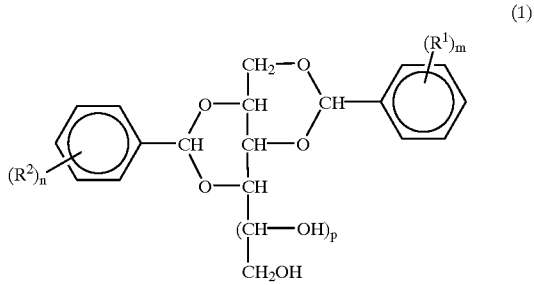

(1)

wherein $R^1$ and $R^2$ are the same or different and each represents an alkyl group having 1 to 4 carbon atoms or a halogen atom, m and n each represent an integer of 0 to 2 and p is 0 or 1.

The present invention also provides a nucleating agent for polyolefin resins, characterized in that the nucleating agent comprises the diacetal of the formula (1), wherein part or the whole of the diacetal is in the form of hexagonal crystals.

The present invention further provides a polyolefin resin composition characterized in that it comprises (a) a polyolefin resin and (b) a nucleating agent, the nucleating agent comprising the diacetal of the formula (1), part or the whole of the diacetal being in the form of hexagonal crystals.

The present invention still further provides a method of molding said polyolefin resin composition, characterized in that it comprises melting the polyolefin resin composition at a temperature which is not lower than a sol-gel transition temperature in heating process (preferably at 200° C. or higher) and which is not higher than 260° C., and molding the melt by injection molding or extrusion molding, wherein the mold temperature in injection molding or the cooling temperature in extrusion molding is set to a temperature in the range of 20 to 70° C.

This molding method of the present invention encompasses a "method for producing extruded pellets" which produces pellets of the resin compositions for injection molding or extrusion molding. That is, the present invention also provides a method of pelletizing the resin composition of the invention, more specifically a method of producing pellets, characterized in that it comprises melting said resin composition at a temperature of 200 to 260° C., extruding the melt and quenching the extrudate to a temperature of 20 to 70° C.

The present invention further provides a molded product produced by molding the above-mentioned resin composition by the foregoing molding method.

The present invention is described below in detail.

Hexagonal Crystals of the Invention

In the present invention, the diacetals represented by the formula (1) are all known compounds and can be easily prepared by conventional methods. According to the present inventors' research, the diacetals prepared by the conventional methods are all in the form of cubic crystals. In other words, the diacetals prepared by conventional methods do not show the features of hexagonal crystals, when analyzed based on the x-ray diffraction patterns. On the other hand, the hexagonal crystals of said diacetal are used in the present invention.

The difference between the hexagonal crystals (A) of the diacetal useful as the nucleating agent of the invention for polyolefin resins and the diacetal cubic crystals (B) is crystallographically clear in terms of x-ray diffractometry.

For example, in the case of 1,3:2,4-bis-O-(p-methylbenzylidene)-D-sorbitol (hereinafter referred to as "MD"), with respect to the unit lattice of hexagonal crystals, a=b=31.5 Angstroms, c=4.3 Angstroms, $\alpha=\beta=90°$ and $\gamma=120°$, whereas with respect to the unit lattice of cubic crystals, a=b=c=13.6 Angstroms, and $\alpha=\beta=\gamma=90°$.

The melting point of these crystals is difficult to accurately measure because they are molecular crystals having various defects. The melting point of said hexagonal crystals is about 275° C. and that of said cubic crystals is about 260° C., and therefore the melting point of the hexagonal crystals are higher by about 15° C. However, the melting points of both crystals often tend to decrease by about 15° C. depending on the size and the degree of lattice defects of the obtained crystals.

Hexagonal crystals are superior in dispersibility in a resin to cubic crystals. When compared under the same molding process temperature condition, hexagonal crystals are much more restrained than cubic crystals from tending to develop fish eyes due to non-dispersed nucleating agent.

Furthermore, molded products produced from a resin composition comprising a polyolefin resin and hexagonal crystals of a diacetal is more excellent than those produced from a resin composition comprising a polyolefin resin and cubic crystals of a diacetal in optical properties (haze value and gloss) and mechanical properties (Young's modulus of elasticity). In addition, molded products containing hexagonal crystals surpass molded products containing cubic crystals in thermal properties, particularly in the rate of nucleation and growth of polyolefin crystals.

Said hexagonal crystals are not formed from a swollen microgel prepared from a diacetal having a crystal structure other than hexagonal crystals, such as cubic crystals, and cylohexane, naphtha or an aliphatic hydrocarbon.

However, said hexagonal crystals can be formed by preparing a gel from a diacetal having other crystal structure than hexagonal crystals and a specific organic solvent and evaporating the organic solvent at a temperature higher than the solidification temperature of the pure solvent without freezing the gel, instead of freeze-drying the gel. Presumably the formation of hexagonal crystals by this method may be attributable to the transition among polymorphic crystal forms. While this is of great interest, the detail is unknown.

The foregoing hexagonal crystals of the invention can be prepared by a process comprising dissolving in an organic solvent with heating a diacetal of the formula (1) obtained by conventional methods (which can be any of other diacetal crystals than hexagonal crystals, such as cubic crystals, aggregated cylinders and other kinds of crystals including orthorhombic, tetragonal, monoclinic and triclinic crystals), cooling the obtained solution, as by allowing the solution to cool, to give a gel, and evaporating the organic solvent from the gel at a temperature higher than the solidification temperature of the organic solvent.

The organic solvent to be used can be any of solvents capable of forming a macrogel due to the gelling action of the diacetal, namely capable of bringing about a state in which a solution loses flow property as a whole. Useful organic solvents include, for example, xylene, toluene, dioxane, dimethylformamide (DMF), dimethylacetamide (DMAc), dimethylsulfoxide (DMSO), cyclohexanone, dichloroethane, ethylene glycol mono $C_1$–$C_4$ alkyl ether, ethylene glycol monoacetate, etc.

Among these solvents, preferred are xylene, dioxane, DMF and ethylene glycol monomethyl ether.

The proportions of the diacetal and the organic solvent to be used are not specifically limited insofar as a gel can be formed, but usually about 1 to about 500 parts by weight, preferably about 3 to about 200 parts by weight, of the organic solvent is used per part by weight of the diacetal.

The above method of dissolution with heating is not specifically limited insofar as it is capable of forming a solution. Generally, however, employable is a method comprising stirring a diacetal in an organic solvent at approximately a boiling point of the organic solvent, e.g. about 40 to about 200° C., preferably about 60 to about 150° C., until a solution is formed. When so required, the solution immediately after dissolution by heating may be filtered to remove insolubles.

The conditions under which the organic solvent is evaporated off from the obtained gel may be, for example, at a temperature higher than the solidification temperature of the organic solvent, preferably about –10° C. to about 80° C., more preferably 0° C. to about 50° C. and under normal pressure or reduced pressure (e.g., about 0.1 to about 20 mmHg).

Nucleating Agent Containing the Hexagonal Crystals of the Invention

For use as a nucleating agent, preferably the obtained hexagonal crystals are finely divided by conventional methods, e.g. using a jet mill (which finely divides the particles by means of their collision in the air) or a rotary pin-mill. The fine particles of hexagonal crystals obtained by pulverization have an average particle size of about 5 to about 200 $\mu$m, preferably about 10 to about 100 $\mu$m. The fine particles may be classified into those having the desired particle size.

According to the present inventors' research, it has been revealed that for use as a nucleating agent for polyolefin resins, the diacetal of the formula (1) may be in the form of hexagonal crystals as a whole, but that even when only a part of the diacetal is in the form of hexagonal crystals, said diacetal similarly shows an excellent nucleating properties.

That is, the hexagonal crystals may be used as admixed with other kinds of crystals. Particularly, it is desirable to use a mixture of the hexagonal crystals of the diacetal of the formula (1) and one or more kinds of crystals, other than hexagonal crystals, of the diacetal of the formula (1) such as cubic crystals.

When such a mixture is used, a mixture of hexagonal crystals (A) and other kinds of crystals such as cubic crystals (B) not only shows a lower melting point compared with the respective melting points of the constituent crystals, but also has greater dispersibility, as a nucleating agent, in the molten resin and dissolved therein at a higher rate. Consequently, such a mixture can be more easily dispersed and dissolved in the resin at a lower temperature compared with the conventional technique, so that the molecules of the nucleating agent are readily dispersed to form a single phase with molecular-dispersion state, with the result that the occurrence of fish eyes due to non-dispersed nucleating agent is suppressed.

For example, in the case of 1,3:2,4-bis-O-(p-methylbenzylidene)-D-sorbitol (MD), this diacetal, when obtained by conventional methods, is in the form of cubic crystals (B) having a melting point of about 260° C. However, when this acetal is mixed with the hexagonal crystals (A) of the present invention, the melting point of the resulting mixture can be freely adjusted to a temperature in the range of from about 275° C. to about 240° C., and this is advantageous from the standpoint of molding process, particularly in respect of the prevention of coloration and fish eyes and in respect of energy-saving, since complete single homogeneous phase can be formed at a slightly higher temperature which is close to the sol-gel transition temperature of the system and therefore the system turns into a single phase at a lower temperature.

When the diacetal is used in the form of a mixture as described above, the proportion of hexagonal crystals (A) and the proportion of other kinds of crystals such as cubic crystals (B) (hereinafter collectively referred to as "C") can be suitably selected from a broad range insofar as the contemplated effects can be achieved. Generally the weight ratio of A/C is approximately 100/0 to 5/95, preferably approximately 95/5 to 5/95, more preferably approximately 95/5 to 15/85. In other words, a good result can be obtained when using, for example, about 19 parts by weight or less, preferably about 0.05 to about 19 parts by weight, more preferably about 0.05 to about 5.7 parts by weight, of other kinds of crystals such as cubic crystals (B), per part by weight of hexagonal crystals (A).

When the ratio is outside of said range, for example, when a nucleating agent consists essentially of cubic crystals (B crystals), the nucleating agent properties diminishes.

The proportions of the crystals as mixed can be selected from a relatively broad range, presumably because the hexagonal crystals (A crystals) present therein trigger a crystal transition from other kinds of crystals such as cubic crystals (B crystals) to a hexagonal crystal (A crystals)-rich system. However, the detail is unknown.

When the hexagonal crystals of the present invention are used as admixed with other kinds of crystals than hexagonal crystals such as cubic crystals, it is preferred that before use, said other kinds of crystals such as cubic crystals be finely divided in the conventional manner, as by a jet mill (which finely divides the particles by means of their collision in the air) or by a rotary pin-mill. The finely divided other kinds of crystals have an average particle size of about 5 to about 200 $\mu$m, preferably about 10 to about 100 $\mu$m. These fine particles may be classified into those having the desired particle size.

When used as a nucleating agent for polyolefin resins, the diacetal of the formula (1), whether in the form of hexagonal crystals alone or as mixed with other kinds of crystals such as cubic crystals as set forth above, may be used singly or in mixture with at least two of the diacetals of the formula (1).

Polyolefin Resin Composition

When said hexagonal crystals are used alone, the amount thereof is about 0.01 to about 3 parts by weight, preferably about 0.05 to about 1.0 part by weight, per 100 parts by weight of the polyolefin resin.

When hexagonal crystals are used as admixed with other kinds of crystals such as cubic crystals, the amount of the mixture to be used is 0.01 to about 3 parts by weight, preferably about 0.05 to about 0.5 part by weight, per 100 parts by weight of the polyolefin resin.

Given below are preferred examples of diacetals to be used in the form of hexagonal crystals alone or in the form of a mixture of hexagonal crystals and other kinds of crystals than hexagonal crystals such as cubic crystals as stated above:

1,3:2,4-bis-O-(3,4-dimethylbenzylidene)-D-sorbitol;

1,3:2,4-bis-O-(p-methylbenzylidene)-D-sorbitol;

1,3:2,4-bis-O-(p-ethylbenzylidene)-D-sorbitol;

1,3-O-(dimethylbenzylidene)-2,4-O-(benzylidene)-D-sorbitol;

1,3-O-(benzylidene)-2,4-O-(dimethylbenzylidene)-D-sorbitol;

1,3:2,4-bis-O-(benzylidene)-D-sorbitol;

1,3:2,4-bis-O-(p-chlorobenzylidene)-D-sorbitol;

1,3-O-(p-chlorobenzylidene)-2,4-O-(-p-methylbenzylidene)-D-sorbitol; and 1,3-O-(p-methylbenzylidene)-2,4-O-(p-chlorobenzylidene)-D-sorbitol.

The diacetal of the formula (1) is added to a polyolefin resin in the form of hexagonal crystals or in the form of a mixture of hexagonal crystals and other kinds of crystals such as cubic crystals as described above. Useful polyolefin resins can be any of those conventionally used in the art.

Thus the term "polyolefin resin(s)" is used herein to mean polyolefin resins having crystallizability and can be any of all kinds of homopolymers of ethylene, all kinds of stereospecific propylene homopolymers, and copolymers prepared from propylene or ethylene and other polymerizable comonomers, insofar as they have a crystallinity of about 20% or more. Polyolefin resins useful in the invention are selectable irrespective of the characteristics of branching structure, density, molecular-weight distribution, kind and degree of stereospecificity, kind of comonomers, catalysts for polymerization and polymerization methods.

Examples of useful polyolefin resins include propylene and ethylene homopolymers and copolymers. The molecular weight of these polyolefin resins can be selected from a broad range and is not specifically limited. Their number average molecular weight is about 10,000 to about 800,000, preferably about 15,000 and about 400,000.

Examples of homopolymers of propylene include stereospecific (syndiotactic or isotactic) polypropylene.

Usable homopolymers of ethylene include, for example, low-density polyethylene (LDPE), medium-density polyethylene, high-density polyethylene, LLDPE (linear LDPE), etc.

In the copolymers prepared from propylene or ethylene and one or more other copolymerizable comonomers, examples of the comonomers are aliphatic or alicyclic olefins of about 2 to about 18 carbon atoms, such as ethylene, propylene, butene, pentene, hexene, heptene, octene, cyclopentene, dicyclohexene, dicycloheptene, etc., vinyl monomers such as vinyl acetate, maleic anhydride, acrylic acid, methacrylic acid, etc. At least one of these comonomers may be used for copolymerization. The proportion of said comonomer to be used for copolymerization can be selected as desired from the range in which the obtained copolymer can maintain the properties of crystalline resins. Generally the proportion of the comonomer is preferably 20% by weight or less, more preferably about 0.5 to about 10% by weight, based on the total weight of the copolymer. The copolymers to be used in the present invention can be any of random copolymers, block copolymers and a mixture of these.

According to the present invention, the polyolefin resin is admixed with the hexagonal crystals of the diacetal of the formula (1) alone or in mixture with other kinds of crystals than the hexagonal crystals, such as cubic crystals, to give a polyolefin resin composition.

Conventional mixing methods can be widely used in the present invention and include, for example, those comprising mixing the components using a Henschel mixer or a similar known powder-mixing device, melting the mixture, extruding the melt, cooling the extrudate and cutting the molded product for pelletization to give the polyolefin resin composition.

When required, the polyolefin resin composition of the invention may contain various additives. Examples of such additives are radical polymerization inhibitors (stabilizers), neutralizing agents, ultraviolet absorbers, flame retardants, light stabilizers, dispersants, lubricants, pigments, dyes, antistatic agenls, fillers, etc.

Radical polymerization inhibitors (stabilizers) to be used in the invention can be any of those conventionally used in the field of polyolefin resins, such as phosphite-type stabilizers, various thiodipropionic acid esters, various phenol-type stabilizers, epoxy compounds and the like. The amount of the radical polymerization inhibitor to be used is about 1 part by weight or less, preferably about 0.005 to about 0.2 part by weight, per 100 parts by weight of the polyolefin resin.

Useful neutralizing agents include those conventionally used in the field of polyolefin resins, such as alkali metal salts or alkaline earth metal salts of fatty acids having 8 to 22 carbon atoms, metal salts of hydroxyoctadecanoic acid or lactic acid (e.g. sodium salt, calcium salt or magnesium salt thereof), hydrogenated rosin soap, and so on. The amount of the neutralizing agent to be used is about 1 part by weight or less, preferably about 0.005 to about 0.2 part by weight, per 100 parts by weight of the polyolefin resin.

An impact resistance improver such as styrene-butadiene rubber (SBR), isobutyrene rubber and like rubbers can be added. The amount of the impact resistance improver to be used is about 60 parts by weight or less, preferably about 5 to about 50 parts by weight, per 100 parts by weight of the polyolefin resin.

Additionally, lubricants such as ethylenebisamide, higher alcohols, aliphatic esters or the like are usable as a processing aid.

Further, aliphatic amines (such as alkanolalkyl-amines of about 12 to about 22 carbon atoms), petroleum resins, coumarone resins or the like may be used in an amount of up to 10 parts by weight per 100 parts by weight of the polyolefin resin.

It is also possible to use other nucleating agents exhibiting a nucleating property, such as a salt of phosphoric acid, talc, salts of acids (e.g. aluminum hydroxy-bis-tert-butyl benzoate), etc.

The foregoing polyolefin resin compositions of the invention have the following remarkable advantages.

(a) The molded product produced from the polyolefin resin composition of the invention is unlikely to have fish eyes owing to the hexagonal crystals of the diacetal of the formula (1) contained therein.

(b) The molded product produced from the polyolefin resin composition of the invention is excellent in optical properties such as haze, gloss and the like and mechanical properties such as rigidity, impact resistance and Young's modulus of elasticity.

(c) The polyolefin resin composition of the invention is advantageous in that the maximum temperature of the peaks of heat evolved by crystallization when cooling the molten resin is high, the crystallization rate is high and the continuous molding cycle time is short.

(d) Molding conditions can be easily optimized by controlling the temperature of molten resin and the temperature of cooled resin during molding, whereby coloration can be prevented and at the same time, and energy can be saved.

Method for Molding the Polyolefin Resin Composition

The present invention also concerns with a method for molding said polyolefin resin composition.

The polyolefin resin composition of the invention can be molded by various molding methods such as injection molding, extrusion molding, blow molding, injection blow molding, air-pressure forming, etc.

Conventional methods of molding diacetal (cubic crystal)-containing compositions will be discussed below. First, a first-stage procedure is carried out which comprises melting a resin composition, uniformly dispersing or dissolving the diacetal, removing the non-dispersed diacetal particles by filtration, extruding the melt and cooling the extrudate to give pellets. Then a second-stage procedure follows which comprises melting the pellets and molding the melt by injection molding, extrusion molding or other molding method to give a final molded product.

Heretofore, there have been two problems in this molding procedure.

One of the problems is the temperature range to be selected as the optimum temperature (T1) in melting the resin composition in the first-stage procedure and as the optimum temperature (T2) in melting the resin composition in the second-stage procedure.

If T1 is set to 240° C. or lower, the cubic crystals of the diacetal are unsatisfactorily dispersed or dissolved, giving pellets which are likely to induce fish eyes due to non-dispersed agglomerate particles. On the other hand, if T1 is set to 270° C. or higher, the resulting molded product is colored yellowish owing to the deterioration of polyolefin or the like although the cubic crystals of the diacetal are well dispersed or dissolved. Consequently, the optimum temperature range of T1 has been heretofore relatively narrow and set to a considerably high temperature region, thereby causing a likelihood of coloring the molded product.

On the other hand, if T2 is set to a temperature below a sol-gel transition temperature in heating process Tgl (usually in the range of about 180 to about 190° C.), the molded product is imparted diminished mechanical properties, particularly lowered modulus in flexure and impact strength. If T2 is set to 270° C. or above, the molded product is colored yellowish. T2 set to 190 to 230° C. results in frequent occurrence of fish eyes due to non-dispersed diacetal (fish eyes arising from poorly dispersed diacetal or agglomerate particles). Consequently it has been heretofore considered that the top priority is to avoid an unsightly appearance derived from fish eyes in the molded product, while disregarding the coloration or alleviating the degree of coloration using an elaborated stabilizer. Thus, at least one of T1 and T2 has been set to 270° C. or above.

On the other hand, according to the present inventors' research, when a nucleating agent comprising the hexagonal crystals of the invention is used, the nucleating agent is better dispersed and dissolved at a higher rate in the molten resin. Consequently the optimum temperatures T1 and T2 in the first-stage and second-stage procedures can be shifted to a lower temperature side of 200 to 260° C., preferably 210 to 250° C., in the neighborhood of Tgl.

As a result, the occurrence of fish eyes was substantially eliminated and a molded product practically free of yellowing was successfully obtained in a stable manner. In addition, since the optimum temperature was shifted to a lower temperature side than the conventional temperature, the consumption of energy was decreased. The molding temperature of polyolefin resins set to 270° C. or above is useful in improving the flowability of molten resin but reached the limit from the viewpoint of heat resistance of resins, and was not justifiable. It is greatly significant that the reduction of melting temperature by 10° C. or more obviates the problem of this deterioration by heat.

Herein, the term "sol-gel transition temperature in heating process Tgl" is defined as a temperature at which a gel completely disappears when heated at a rate of 1° C./min, the gel being produced by maintaining the system (resin composition) at 250° C. for 10 minutes to give a homogeneous melt, and then cooling the melt, followed by maintaining the melt at a temperature of 150° C. for 20 minutes for gelation. The term "sol-gel transition temperature in cooling process Tg" used herein is defined as a temperature at which a rapid increase in storage modulus G' is initiated when the system (resin composition) is cooled from 250° C. at a rate of 1° C./min.

Said Tgl and Tg can be easily determined by measuring the dynamic viscoelasticity using a rheometer (e.g., "MR-500 SOLIQUID METER", product of RHEOLOGY Kabushiki Kaisha.).

In the case of a polyolefin containing 0.2 to 0.3 weight % of a diacetal prepared by the conventional method, Tgl is usually in the range of 180 to 190° C. although slightly variable depending on the type of resins.

Next, an optimum condition for crystallization from a molten resin, which is the second problem in the molding method, is considered. For example, in the case of said homopolymers or copolymers of propylene, a temperature Tv showing the highest crystallization rate (i.e., optimum crystallization temperature) falls in the temperature range sufficiently higher than a glass transition temperature close to 0° C. and sufficiently lower than the melting point thereof close to 160° C., namely in the range of 100 to 120° C. Generally the quenching temperature in injection molding should be set to this range. Further, in the case of homopolymers or copolymers of ethylene, an optimum crystallization temperature Tv, although depending on the kind of resins, is lower than the above-mentioned range by 20 to 30° C. and is usually in the range of about 80 to about 100° C.

The temperature Tg at which gelation takes place (sol-gel transition temperature in cooling process) due to the precipitation of diacetal crystals and formation of network is generally higher than Tv.

Concerning the morphological change which the polyolefin resin composition containing a diacetal nucleating agent undergoes depending on the temperature, it is presumed as follows. When a high temperature sol in which the diacetal crystals are uniformly dispersed is cooled to Tg, the diacetal forms a fibrous network structure to give a gel, and when the temperature is further lowered, the crystallization of polyolefin is commenced at the interface between the network structure and the molten polyolefin.

Consequently, the factor that causes a diacetal to act as a nucleating agent is considered to be the network structure formed by the diacetal, and therefore it has been considered that the desirable molding condition is such that the molten resin is first quenched to a gel-forming temperature range, which is above Tv and below Tg, to form a network of diacetal and is further quenched to the optimum polyolefin resin crystallization temperature Tv.

However, when the nucleating agent comprising. the hexagonal crystals of the present invention is used, it has been revealed that when the molten resin is rapidly cooled (namely quenched) at one time to a temperature range of not higher than 70° C. but not lower than 20° C., which is by far lower than Tv, the maximum resin improving effect (e.g. lowest haze value, greatest Tc and highest rigidity) and the highest molding efficiency (amount of moldings produced per hour) can be achieved. If the resin is quenched to below 20° C., the crystallization rate of the resin becomes decreased, and hence it is impractical. The above result has not been fully clarified yet but is a surprising new discovery.

Thus, the present invention provides a method for molding the polyolefin resin composition of the invention by injection or extrusion molding, characterized in that the method comprises the steps of melting the polyolefin resin composition at a temperature which is higher than the sol-gel transition temperature in heating process (preferably 200° C. or above) and which is not higher than 260° C., preferably at a temperature of 210 to 250° C., and carrying out a molding operation wherein the cooling temperature, such as the mold temperature in injection molding or the chill roll temperature in extrusion molding, is set to a temperature in the range of 20 to 70° C.

In the case of injection molding, the molding operation is carried out by repeating a molding cycle which consists of a series of steps, i.e., mold clamping, injection, dwell, cooling, mold opening and removal from the mold. In this cycle, the melting temperature during the injection step is set to the temperature range between the sol-gel transition temperature in heating process and 260° C. as set forth above, and the cooling temperature is set to the range of 20 to 70° C., whereby a molded product having excellent properties is obtained.

In the case of extrusion molding, the composition is molded by extrusion molding through an extruder, a die and a take-up unit to continuously form a sheet or a film having a uniform cross-sectional shape. In this extrusion procedure, the melting temperature condition in the extruder and the die is set to a temperature range between the sol-gel transition temperature in heating process and 260° C. (particularly 200 to 260° C.) as described above, and the cooling temperature is set to 20 to 70° C., whereby a molded product having excellent properties is obtained.

Further, when said melting temperature and said cooling temperature are employed in preparing pellets of polyolefin resin composition, pellets are obtained free of non-dispersed diacetal and yellowing. Thus, the present invention also provides a method for forming pellets of the polyolefin resin composition of the invention, characterized in that the method comprises the steps of melting the polyolefin resin composition at a temperature of 200 to 260° C., extruding the melt and cooling the extrudate to a temperature of 20 to 70° C.

In the molding method of the invention by extrusion or injection molding, the polyolefin resin composition of the invention can be used in the form of pellets having the final make-up (namely, the pellets produced from the composition containing the above-specified amount of the nucleating agent of the invention) or in the form of a non-pelletized powder or, when required, in the form of masterbatch pellets produced using the nucleating agent of the invention in a proportion of 1 to 15% by weight based on the polyolefin resin.

In either of the injection molding or extrusion molding, the polyolefin resin composition of the invention in any of said forms is first melted at a temperature higher than the sol-gel transition temperature in heating process, particularly about 20° C. higher than said sol-gel transition temperature, usually at a temperature of 200 to 260° C. In particular, it is preferable that in the case of homopolymers or copolymers of propylene, the composition be melted at about 200 to about 260° C. and in the case of homopolymers or copolymers of ethylene, the composition be melted at about 200 to about 240° C.

Next, the molding operation is carried out by quenching the mold for injection molding or the chill roll for extrusion molding to a temperature in the range of 20 to 70° C., preferably 25 to 65° C., more preferably 25 to 50° C. That is to say, according to the invention, the melt at 200 to 260° C. is introduced into the mold or the chill roll set to 20 to 70° C., thereby carrying out cooling to a temperature range of 20 to 70° C. at one time, namely so-called quenching (rapid cooling).

This molding method of the invention has the following advantages.

(a) The molding cycle time is shortened and the moldability is excellent.

(b) Moreover, the temperature of the molten resin is relatively low, and it is beneficial in terms of energy as well.

(c) Other advantages include the prevention of the molded product from coloration due to deterioration of the resin and the inhibition of fish eyes from occurring due to non-dispersed diacetal.

Polyolefin Resin Molded Product

The invention also provides a molded article produced by molding the above-mentioned polyolefin resin composition of the invention or the pellets produced from the composition by the foregoing molding method.

The molded products of the invention include any of those conventionally produced from polyolefin resins by molding methods such as injection molding, extrusion molding, blow molding, injection-blow molding or air-pressure forming. Examples thereof are cases, containers, connectors, syringes, various lids, sheets, films, etc.

The molded products thus obtained from the polyolefin resin composition of the invention have the feature of containing the hexagonal crystals of the diacetal of the formula (1) and due to this feature, are superior to the molded products prepared from the polyolefin resin composition containing the cubic crystals of said diacetal in optical properties (haze value and gloss) and mechanical properties (flexural modulus, impact strength and Young's modulus of elasticity) and in thermal properties (HDT, heat distortion temperature) with virtually no fish eye and substantially free of yellowing, insuring transparent, colorless, aesthetically attractive finish.

EXAMPLES

The present invention will be described in greater detail with reference to the following Examples.

The fact that A crystals and B crystals of the diacetal used in the Examples and Comparative Examples were hexagonal and cubic crystals, respectively, was confirmed by obtaining two-dimensional x-ray diffraction profiles ranging from a small angle to a wide angle range by simultaneously measuring the SAXS (small angle x-ray scattering) profile and WAXD (wide angle x-ray diffraction) profile in the conventional manner, and determining the lattice constant of the unit lattice by the analysis of the profiles.

Examples 1–1 to 1–4 and Comparative Examples 1–1 to 1–6

(a) Preparation of Hexagonal and Cubic Crystals of Diacetal

The hexagonal crystals (A crystals) and cubic crystals (B crystals) used in the Examples and Comparative Examples are the diacetal crystals prepared by the following method.

1) A crystals:

According to the conventional production method, 1,3:2,4-bis-O-(p-methylbenzylidene)-D-sorbitol (MD) was obtained as cubic crystals (B crystals) in a yield of 82% using cyclohexane as a hydrophobic organic solvent, methanol as a polar solvent and sulfuric acid as an acid catalyst, and feeding D-sorbitol and p-methylbenzaldehyde in a molar ratio of 1:2 while removing the condensation water from the system (i.e., the method of preparing a diacetal as disclosed in Japanese Unexamined Patent Publication No. 231488/1990).

A 0.1 kg portion of MD was dispersed in 20 kg of xylene and dissolved therein with heating at 140° C. After filtering the solution, the filtrate was allowed to cool, giving a gel. The gel was dried by evaporating the xylene from the gel under vacuum at room temperature, giving hexagonal crystals (A crystals). Said A crystals were finely divided (average particle size 40 μm) using a jet grinding mill (product of Hosokawa Micron Co., Ltd.).

2) B crystals:

MD in a cubic crystal form (B crystals) obtained by the above-mentioned conventional production method (the method of preparing a diacetal as disclosed in Japanese Unexamined Patent Publication No. 231488/1990) was finely divided (average particle size 42 μm) using a jet grinding mill (product of Hosokawa Micron Co., Ltd.).

(b) Preparation and Molding of Polyolefin Resin Composition

The polyolefin resin used in the Examples and the Comparative Examples is a random polypropylene (r-PP, an ethylene-propylene copolymer having an ethylene content of 1.5% by weight, melt index MI=6, number average molecular weight=$6.0 \times 10^4$).

The random polypropylene (100 parts by weight), 0.05 part by weight of calcium stearate and MD either in the form of finely divided hexagonal crystals (A) or in the form of a mixture of said hexagonal crystals (A) and cubic crystals (B) (in the amount shown below in Table 1 (by weight)) were dry-blended using a Henschel mixer for 10 minutes. Then the mixture was molded by low-temperature extrusion molding at 200° C., and cooled with water to 30° C. to give strands. The strands were cut into pellets.

The pellets were charged from the hopper of an injection molding machine. Thereafter the melt was extruded at 220° C. and fed under a pressure to a mold, followed by mold clamping. The mold cooling temperature was set to 50° C. by circulating a heat transfer medium having a temperature of 50° C. In this way, sheet having a thickness of 1.0 mm was obtained.

The properties of the sheet obtained by the above injection molding were evaluated by the following methods.

(1) Maximum Temperature (Tc) at Peaks of Heat Evolved in Crystallization

Measured by a differential scanning calorimetry (DSC), wherein the sheet was melted with heating at 240° C. for 5 minutes, and then the melt was cooled at a rate of 10° C./min.

The higher the value of Tc is, the lower the degree of supercooling in crystallization of polyolefin resin is, and thus the higher the rate of crystallization is. Consequently, the higher the value of Tc is, the shorter the cycle time of continuous molding is. Hence it is desirable.

(2) Haze

Measured according to JIS K 6717 and 6714

(3) Flexural Modulus

Measured according to ASTM D-790.

(4) Occurrence of yellowing o: yellowing did not occur x: yellowing occurred (5) Occurrence of fish eyes Ten injection-molded sheets were visually inspected and evaluated according to the following criteria.

o: There was not a single sheet having fish eyes due to non-dispersed diacetal agglomerates.

x: At least one sheet was found to have fish eyes due to non-dispersed diacetal agglomerates.

The results of evaluation are shown in Table 1.

TABLE 1

| | Amount of diacetal (wt part) | | Properties of PP sheet | | | | |
|---|---|---|---|---|---|---|---|
| | A | B | Tc (° C.) | Haze (%) | Flexural Modulus (kg/mm$^2$) | Yellowing | FE* |
| Ex. | | | | | | | |
| 1-1 | 0.3 | 0 | 131 | 8.5 | 115 | o | o |
| 1-2 | 0.2 | 0 | 130 | 8.3 | 115 | o | o |
| 1-3 | 0.1 | 0.1 | 131 | 8.8 | 116 | o | o |
| 1-4 | 0.1 | 0.2 | 133 | 8.5 | 117 | o | o |
| Comp. Ex. | | | | | | | |
| 1-1 | 0 | 0 | 103 | 56.0 | 79 | o | o |
| 1-2 | 0 | 0.2 | 118 | 11.5 | 108 | o | x |
| 1-3 | 0 | 0.3 | 119 | 12.5 | 108 | o | x |
| 1-4 | 0.3 | 0 | 131 | 12.3 | 115 | o | o |
| 1-5 | 0.3 | 0 | 131 | 12.0 | 100 | o | o |
| 1-6 | 0.3 | 0 | 131 | 8.8 | 115 | x | o |

*FE: Fish eyes

In Examples 1-3 and 1-4, finely divided A crystals and B crystals were used as pre-mixed together.

The mixtures of A crystals and B crystals of MD used in Examples 1-3 and 1-4 had melting points of 250° C. and 241° C., respectively.

In Comparative Example 1-4, the mold-cooling temperature was set to 110° C.

In Comparative Example 1-5, the temperature of the resin to be injected was set to 180° C. which was lower than Tgl (190° C.) and the mold-cooling temperature was set to 50° C.

In Comparative Example 1-6, the temperature of the resin to be injected was set to 275° C. and the mold-cooling temperature was set to 50° C.

The IZOD impact strength (measured according to ASTM D-256) was 1.8 kg·cm/cm$^2$ in Comparative Example 1-5 and 3.2 kg·cm/cm$^2$ in Example 1-1.

Examples 2-1 to 2-4 and Comparative Examples 2-1 to 2-3

The procedure of Example 1 (a) was repeated except that 1,3:2,4-bis-O-(3,4-dimethylbenzylidene)-D-sorbitol was used in place of 1,3:2,4-bis-O-(p-methyl-benzylidene)-D-sorbitol, thereby producing A crystals and B crystals.

Sheets of 1.0 mm thickness were obtained by injection molding in the same manner as in Example 1 (b) with the exception of using the above crystals either alone or in mixture in the amount shown in Table 2.

The obtained sheets were evaluated in the same manner as in Example 1. The results of the evaluation are shown in Table 2.

TABLE 2

| | Amount of diacetal (wt. part) | | Properties of PP sheet | | |
|---|---|---|---|---|---|
| | A | B | Tc (° C.) | Haze (%) | Flexural Modulus (kg/mm²) |
| Example | | | | | |
| 2-1 | 0.6 | 0 | 131 | 8.0 | 120 |
| 2-2 | 0.1 | 0 | 128 | 9.5 | 115 |
| 2-3 | 0.1 | 0.1 | 131 | 8.8 | 116 |
| 2-4 | 0.1 | 0.2 | 130 | 8.0 | 120 |
| Comparative Example | | | | | |
| 2-1 | 0 | 0.1 | 120 | 15.5 | 108 |
| 2-2 | 0 | 0.3 | 119 | 12.5 | 108 |
| 2-3 | 0.1 | 0.2 | 130 | 12.8 | 110 |

The mold temperature in Comparative Example 2-3 is 120° C.

Test Example 1
(a) Preparation of Diacetal A Crystals and B Crystals

A reaction was carried out according to the conventional method (the method disclosed in Japanese Unexamined Patent Publication No. 231488/1990) using benzaldehyde, p-ethylbenzaldehyde, p-chlorobenzaldehyde or an equimolar mixture of benzaldehyde and 3,4-dimethylbenzaldehyde, in place of p-methylbenzaldehyde used in the production of Example 1 (a), thereby producing 4 kinds of diacetals shown below. These diacetals are all in the form of cubic crystals.

These B crystals were finely divided using a jet grinding mill (Hosokawa Micron Co., Ltd.) (an average particle size of 40±5 μm).
(1) H-DBS:
    1,3:2,4-bis-O-(benzylidene)-D-sorbitol
(2) Et-DBS:
    1,3:2,4-bis-O-(p-ethylbenzylidene)-D-sorbitol
(3) Cl-DBS
    1,3:2,4-bis-O-(p-chlorobenzylidene)-D-sorbitol
(4) H, DMe-DBS:
    A 1:1 mixture of 1,3-O-(benzylidene)-2,4-O-(3,4-dimethylbenzylidene)-D-sorbitol and 1,3-O-(3,4-dimethyl-benzylidene)-2,4-O-(benzylidene)-D-sorbitol.

A 0.1 kg portion of the diacetal in the form of cubic crystal (before being finely divided) which was prepared by the above method was dispersed in 20 kg of xylene and dissolved therein with heating at 140° C. The solution was filtered, and the filtrate was allowed to cool, giving a gel. The gel was dried by evaporating xylene from the gel under vacuum at room temperature, giving hexagonal crystals (A crystals).

These A crystals were finely divided using a jet grinding mill (Hosokawa Micron Co., Ltd.) (an average particle size of 40±5 μm).
(b) Observation of Crystal Forming Rate The diacetal A and B crystals obtained above were placed on a melt of isotactic polypropylene at 147° C., 143° C. and 140° C., respectively. While maintaining each temperature for 10 minutes, observation was made under a microscope. When crystals of isotactic polypropylene were formed in the interface between the diacetal and the melt, the result was shown as "○" in Table 3, whereas when crystal formation was not observed, it was marked "x" in Table 3.

TABLE 3

| No. | Kind of diacetal | Crystal form | PP Crystal formation | | |
|---|---|---|---|---|---|
| | | | 147° C. | 143° C. | 140° C. |
| 1 | H-DBS | A | ○ | ○ | ○ |
| 2 | H-DBS | B | x | x | ○ |
| 3 | Et-DBS | A | ○ | ○ | ○ |
| 4 | Et-DBS | B | x | x | ○ |
| 5 | Cl-DBS | A | ○ | ○ | ○ |
| 6 | Cl-DBS | B | x | x | ○ |
| 7 | H-, DMe-DBS | A | ○ | ○ | ○ |
| 8 | H-, DMe-DBS | B | x | x | ○ |

It is apparent from the results of Table 3 that A crystals and B crystals both have the properties of nucleating agents and that A crystals are superior to B crystals in the ability of nucleating agents, particularly in the rate of forming the polypropylene crystals.

Reference Example 1

Conventional methods for producing diacetals are basically classified into two types. Stated more specifically, (1) a dehydration condensation method using a combination of a hydrophobic solvent and a polar solvent as proposed by Kobayashi et al (e.g., the method disclosed in Japanese Examined Patent Publication No. 43748/1973) and (2) a classical water solvent method (e.g., the method disclosed in Japanese Examined Patent Publication No. 7460/1972). Also proposed is (3) a gel state high concentration method which is a modification of the method (1) (e.g., the method disclosed in Japanese Unexamined Patent Publication No. 149789/1989). According to the present inventors' tests, the diacetal crystals produced by any of these methods were in the form of cubic crystals (B).

Commercially available diacetals and their crystal form are tabulated below in Table 4.

The abbreviations of diacetals shown in Table 4 refer to the following compounds.
(1) p-Methyl-DBS
    1,3:2,4-bis-O-(p-methylbenzylidene)-D-sorbitol
(2) 3,4-Dimethyl-DBS:
    1,3:2,4-bis-O-(3,4-dimethylbenzylidene)-D-sorbitol
(3) p-Ethyl-DBS
    1,3:2,4-bis-O-(p-ethylbenzylidene)-D-sorbitol
(4) DBS
    1,3:2,4-bis-O-(benzylidene)-D-sorbitol.

TABLE 4

| No. | Commercial product | Manufacturer | Kind of diacetal | Crystal form |
|---|---|---|---|---|
| 1 | Gel All MD | New Japan Chemical Co., Ltd. | p-Methyl-DBS | B |
| 2 | Gel All DX | New Japan Chemical Co., Ltd. | 3,4-Dimethyl-DBS | B |
| 3 | NC-4 | Mitsui Toatsu Chemicals Inc. | p-Ethyl-DBS | B |
| 4 | EC-1 | EC *1 | DBS | B |
| 5 | Millad 3905 | Milliken *2 | DBS | B |

TABLE 4-continued

| No. | Commercial product | Manufacturer | Kind of diacetal | Crystal form |
|---|---|---|---|---|
| 6 | Millad 3940 | Milliken *2 | p-Methyl-DBS | B |
| 7 | Dissorben | Roquette *3 | DBS | B |

*1 EC Chemical Industry Co., Ltd.
*2 Milliken Research Corporation
*3 Roquette Freres As apparent from Table 4, the diacetals prepared by the conventional methods are all in the form of cubic crystals (B).

We claim:

1. Hexagonal crystal of a diacetal represented by the formula (1)

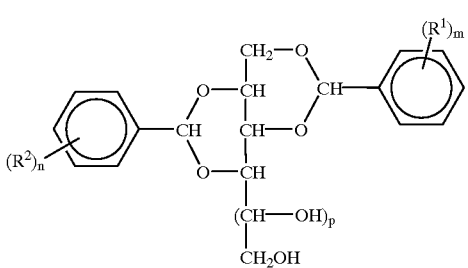

(1)

wherein $R^1$ and $R^2$ are the same or different and each represents an alkyl group having 1 to 4 carbon atoms or a halogen atom, each of m and n represents an integer of 0 to 2 and p represents 0 or 1.

2. The hexagonal crystals according to claim 1, wherein the diacetal of the formula (1) is at least one member selected from the group consisting of 1,3:2,4-bis-O-(3,4-dimethylbenzylidene)-D-sorbitol, 1,3:2,4-bis-O-(p-methylbenzylidene)-D-sorbitol, 1,3:2,4-bis-O-(p-ethylbenzylidene)-D-sorbitol, 1,3-O-(dimethylbenzylidene)-2,4-O-(benzylidene)-D-sorbitol, 1,3-O-(benzylidene)-2,4-O-(dimethylbenzylidene)-D-sorbitol, 1,3:2,4-bis-O-(benzylidene)-D-sorbitol, 1,3:2,4-bis-O-(p-chlorobenzylidene)-D-sorbitol, 1,3-O-(p-chlorobenzylidene)-2,4-O-(p-methylbenzylidene)-D-sorbitol and 1,3-O-(p-methylbenzylidene)-2,4-O-(p-chlorobenzylidene)-D-sorbitol.

3. A nucleating agent for polyolefin resins, characterized in that the nucleating agent comprises a diacetal represented by the formula (1)

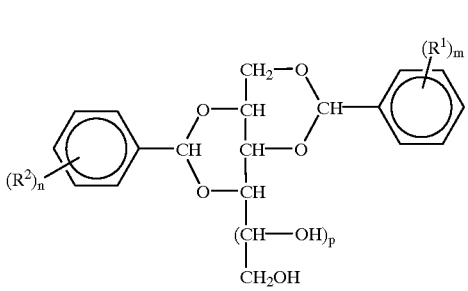

(1)

wherein $R^1$ and $R^2$ are the same or different and each represents an alkyl group having 1 to 4 carbon atoms or a halogen atom, each of m and n represents an integer of 0 to 2 and p represents 0 or 1, wherein part or the whole of said diacetal is in the form of hexagonal crystals.

4. The nucleating agent for polyolefin resins according to claim 3, which comprises the hexagonal crystals of the diacetal of the formula (1) or a mixture of hexagonal crystals of the diacetal of the formula (1) and other kinds of crystals than the hexagonal crystals, the amount of other kinds of crystals being 19 parts by weight or less per part by weight of the hexagonal crystals.

5. The nucleating agent for polyolefin resins according to claim 3 or 4, wherein the diacetal of the formula (1) is at least one member selected from the group consisting of 1,3:2,4-bis-O-(3,4-dimethylbenzylidene)-D-sorbitol, 1,3:2,4-bis-O-(p-methylbenzylidene)-D-sorbitol, 1,3:2,4-bis-O-(p-ethylbenzylidene)-D-sorbitol, 1,3-O-(dimethylbenzylidene)-2,4-O-(benzylidene)-D-sorbitol, 1,3-O-(benzylidene)-2,4-O-(dimethylbenzylidene)-D-sorbitol, 1,3:2,4-bis-O-(benzylidene)-D-sorbitol, 1,3:2,4-bis-O-(p-chlorobenzylidene)-D-sorbitol, 1,3-O-(p-chlorobenzylidene)-2,4-O-(p-methylbenzylidene)-D-sorbitol and 1,3-O-(p-methylbenzylidene)-2,4-O-(p-chlorobenzylidene)-D-sorbitol.

6. A polyolefin resin composition comprising a polyolefin resin and a nucleating agent, characterized in that the nucleating agent comprises a diacetal represented by the formula (1)

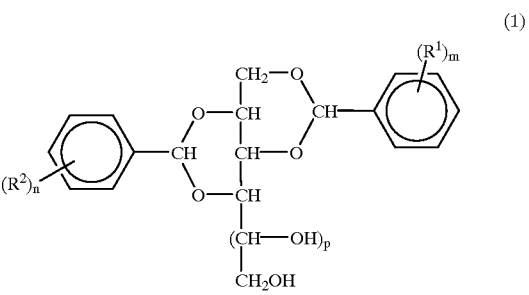

(1)

wherein $R^1$ and $R^2$ are the same or different and each represents an alkyl group having 1 to 4 carbon atoms or a halogen atom, each of m and n represents an integer of 0 to 2 and p represents 0 or 1, wherein part or the whole of said diacetal is in the form of hexagonal crystals.

7. The polyolefin resin composition according to claim 6 wherein the nucleating agent comprises the hexagonal crystals of the diacetal of the formula (1) or a mixture of the hexagonal crystals of the diacetal of the formula (1) and other kinds of crystals than the hexagonal crystals, the amount of other kinds of crystals being 19 parts by weight or less per part by weight of the hexagonal crystals.

8. A The polyolefin resin composition according to claim 6 or 7 wherein the diacetal of the formula (1) is at least one member selected from the group consisting of 1,3:2,4-bis-O-(3,4-dimethylbenzylidene)-D-sorbitol, 1,3:2,4-bis-O-(p-methylbenzylidene)-D-sorbitol, 1,3:2,4-bis-O-(p-ethylbenzylidene)-D-sorbitol, 1,3-O-(dimethylbenzylidene)-2,4-O-(benzylidene)-D-sorbitol, 1,3-O-(benzylidene)-2,4-O-(dimethylbenzylidene)-D-sorbitol, 1,3:2,4-bis-O-(benzylidene)-D-sorbitol, 1,3:2,4-bis-O-(p-chlorobenzylidene)-D-sorbitol, 1,3-O-(p-chlorobenzylidene)-2,4-O-(p-methylbenzylidene)-D-sorbitol and 1,3-O-(p-methylbenzylidene)-2,4-O-(p-chlorobenzylidene)-D-sorbitol.

9. The polyolefin resin composition according to claim 6, wherein the nucleating agent is used in an amount of 0.01 to 3 parts by weight per 100 parts by weight of the polyolefin resin.

10. A polyolefin resin molded product comprising a polyolefin resin and a nucleating agent, characterized in that the nucleating agent comprises a diacetal represented by the formula (1)

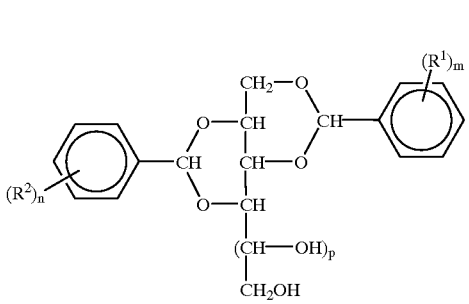

(1)

wherein $R^1$ and $R^2$ are the same or different and each represents an alkyl group having 1 to 4 carbon atoms or a halogen atom, each of m and n represents an integer of 0 to 2 and p represents 0 or 1, wherein part or the whole of said diacetal is in the form of hexagonal crystals.

11. The polyolefin resin molded product according to claim 10, wherein the nucleating agent comprises the hexagonal crystals of the diacetal of the formula (1) or a mixture of the hexagonal crystals of the diacetal of the formula (1) and other kinds of crystals than the hexagonal crystals, the amount of other kinds of crystals being 19 parts by weight or less per part by weight of the hexagonal crystals.

12. The polyolefin resin molded product according to claim 10 or 11, wherein the diacetal of the formula (1) is at least one member selected from the group consisting of 1,3:2,4-bis-O-(3,4-dimethylbenzylidene)-D-sorbitol, 1,3:2,4-bis-O-(p-methylbenzylidene)-D-sorbitol, 1,3:2,4-bis-O-(p-ethylbenzylidene)-D-sorbitol, 1,3-O-(dimethylbenzylidene)-2,4-O-(benzylidene)-D-sorbitol, 1,3-O-(benzylidene)-2,4-O-(dimethylbenzylidene)-D-sorbitol, 1,3:2,4-bis-O-(benzylidene)-D-sorbitol, 1,3:2,4-bis-O-(p-chlorobenzylidene)-D-sorbitol, 1,3-O-(p-chlorobenzylidene)-2,4-O-(p-methylbenzylidene)-D-sorbitol and 1,3-O-(p-methylbenzylidene)-2,4-O-(p-chlorobenzylidene)-D-sorbitol.

13. The molded product according to any one of claims 10 or 11, wherein the nucleating agent is used in an amount of 0.01 to 3 parts by weight per 100 parts by weight of the polyolefin resin.

14. A method of molding the polyolefin resin composition of claim 6 by injection or extrusion molding, characterized in that the method comprising melting the polyolefin resin composition at a temperature between the sol-gel transition temperature in heating process and 260° C., and molding the melt by injection molding or extrusion molding, wherein the mold temperature in injection molding or the cooling temperature in extrusion molding is set to the range of 20 to 70° C.

15. A method for molding the polyolefin resin composition of claim 6 to give pellets, characterized in that the method comprises melting said polyolefin resin composition at a temperature between the sol-gel transition temperature in heating process and 260° C., extruding the melt and cooling the extrudate at a temperature of 20 to 70° C.

16. A polyolefin resin composition comprising a polyolefin resin and a nucleating agent, the polyolefin resin composition being obtainable by melting a mixture comprising the polyolefin resin and the nucleating agent, extruding the melt, cooling the extrudate and cutting the molded product for pelletization, wherein the nucleating agent comprises a diacetal represented by the formula (1)

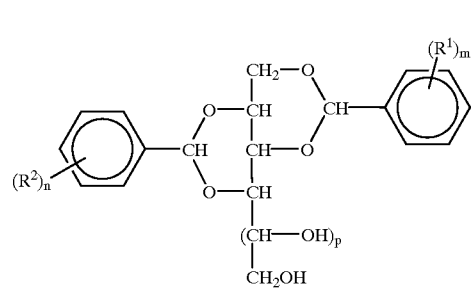

(1)

wherein $R^1$ and $R^2$ are the same or different and each represents an alkyl group having 1 to 4 carbon atoms or a halogen atom, each of m and n represents an integer of 0 to 2 and p represents 0 or 1, wherein part or the whole of said diacetal is in the form of hexagonal crystals.

17. A molded article comprising a polyolefin resin and a nucleating agent, the molded article being obtainable by molding a polyolefin resin composition by means of a molding method by injection molding or extrusion molding, said polyolefin resin composition being prepared by melting a mixture comprising the polyolefin resin and the nucleating agent, extruding the melt, cooling the extrudate, cutting the resulting molded product for pelletization, the nucleating agent comprising a diacetal represented by the formula (1)

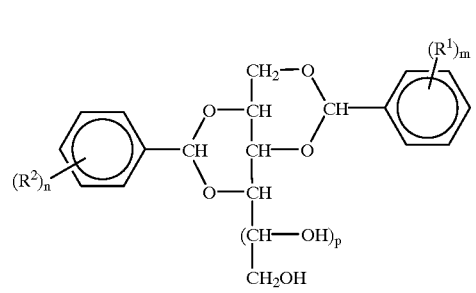

(1)

wherein $R^1$ and $R^2$ are the same or different and each represents an alkyl group having 1 to 4 carbon atoms or a halogen atom, each of m and n represents an integer of 0 to 2 and p represents 0 or 1, wherein part or the whole of said diacetal is in the form of hexagonal crystals, and the molding method being a method comprising the steps of melting said polyolefin resin composition at a temperature between the sol-gel transition temperature in heating process and 260° C., and molding the melt by injection molding or extrusion molding, wherein the mold temperature in injection molding or the cooling temperature in extrusion molding is set to the range of 20 to 70° C.

18. A process for preparing hexagonal crystal of a diacetal represented by the formula (1)

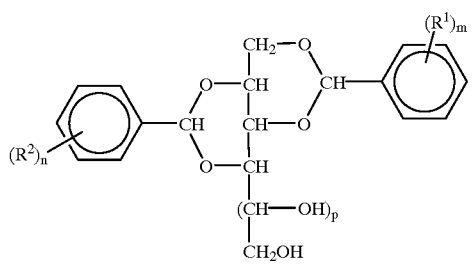

wherein $R^1$ and $R^2$ are the same or different and each represents an alkyl group having 1 to 4 carbon atoms or a halogen atom, each of m and n represents an integer of 0 to 2 and p represents 0 or 1, the process comprising dissolving in an organic solvent with heating the diacetal represented by the formula (1) which can be any of other diacetal crystals than hexagonal crystals, cooling the obtained solution to give a gel and evaporating the organic solvent from the gel at a temperature higher than the solidification temperature of the organic solvent.

* * * * *